United States Patent [19]

Fukunishi

[11] Patent Number: 4,998,971

[45] Date of Patent: Mar. 12, 1991

[54] ELECTRONIC ENDOSCOPE APPARATUS CAPABLE OF OBSERVING LASER-ILLUMINATED BIOLOGICAL BODY PORTION

[75] Inventor: Souhei Fukunishi, Tochigi, Japan

[73] Assignee: Kabushiki Kaisha Toshiba, Kawasaki, Japan

[21] Appl. No.: 540,003

[22] Filed: Jun. 19, 1990

[30] Foreign Application Priority Data

Jun. 22, 1989 [JP] Japan .................................. 1-158400

[51] Int. Cl.$^5$ .............................................. A61B 1/04
[52] U.S. Cl. ......................................... 128/6; 358/98; 606/18
[58] Field of Search ...................... 128/4, 6; 358/98; 606/18, 46

[56] References Cited

U.S. PATENT DOCUMENTS

| | | | |
|---|---|---|---|
| 4,211,229 | 7/1980 | Wurster | 606/18 X |
| 4,580,559 | 4/1986 | L'Esperance | 606/18 X |
| 4,597,380 | 7/1986 | Raif et al. | 128/6 |
| 4,845,555 | 7/1989 | Yabe et al. | 358/98 |
| 4,901,718 | 2/1990 | Bille et al. | 606/18 X |

FOREIGN PATENT DOCUMENTS

| | | |
|---|---|---|
| 62-129047 | 6/1987 | Japan . |
| 62-142311 | 9/1987 | Japan . |
| 1-265934 | 10/1989 | Japan . |

*Primary Examiner*—William H. Grieb
*Attorney, Agent, or Firm*—Foley & Lardner

[57] ABSTRACT

To prevent a halation phenomenon from an endoscopic image of a laser-illuminated body cavity of a biological body under medical examination, an electronic endoscope apparatus comprises an electronic scope unit and a main endoscope unit coupled to the electronic scope unit. The electronic scope unit includes: a laser mirror upon which laser light reflected from the laser-illuminated body cavity of the biological body under medical examination is incident, for refracting a first light component having a laser light wavelength of the incident laser light and also for passing therethrough a second light component having a visible light wavelength other than the laser light wavelength; a first image sensor for receiving the first light component refracted from the laser mirror; a second image sensor for directly receiving the second light component passing through the laser mirror to produce a visible light image signal; and, an ND (neutral density) filter positioned on a light-receiving surface of the first image sensor, for lowering brightness of the first light component having the laser light wavelength, thereby producing a laser light image signal from the first image sensor. The main endoscope unit processes both the laser light image signal and visible light image signal to display an endoscopic image of the laser-illuminated body cavity and of a body portion around the laser-illuminated body cavity without any halation phenomenon.

12 Claims, 4 Drawing Sheets

ELECTRONIC ENDOSCOPE APPARATUS CAPABLE OF OBSERVING LASER-ILLUMINATED BIOLOGICAL BODY PORTION

BACKGROUND OF THE INVENTION

1. Field of the Invention

The present invention relates to an electronic endoscope apparatus capable of observing a laser-illuminated biological body portion without any halation phenomenon.

2. Description of the Related Art

Various types of electronic endoscope apparatus employing an electronic scope through which a biological body portion is illuminated, and an image sensor to produce an endoscopic image of the illuminated body portion, have been developed and are commercially available in the medical electronic field.

The aims of such electronic endoscope apparatuses are to observe an organ within a body cavity of the biological body, and also to cure the biological body in accordance with the endoscope laser curing methods, e.g., the lasing, and dissection.

As is known, in the curing observation by the laser illumination, the brightness of the laser reflected from the laser-illuminated portion of the biological body is extremely higher than that reflected from another portion around this laser-illuminated biological body portion. As a result, if the laser light reflected from the laser-illuminated biological body portion is directly received by the image sensor and the endoscopic image thereof is displayed by processing the image signal derived from this image sensor, there is induced a halation phenomenon in the endoscopic image of the laser-illuminated biological body portion, in a specific case, over the entire endoscopic image of the observed biological body.

To solve this halation difficulty, one conventional solution has been proposed, for instance, in Japanese KOKAI (Disclosure) patent application No. 62-129047 opened on June 11, 1987 and Japanese KOKAI utility model application No. 62-14231 opened on Sept. 8, 1987. That is, the laser cut filter, e.g., an infrared cut filter is positioned in the optical system employed within the distal end unit of the electronic scope so as to prevent the laser light component to be incident upon the image sensor.

Although such a halation problem can be solved by employing the laser cut filter in these conventional electronic endoscope apparatuses, another problem may newly occur. In other words, when the optical image formed by cutting out the laser light component is incident upon this image sensor to whereby display an endoscopic image of the biological body, in which the conditions of the laser-illuminated biological body portion cannot be observed from the endoscopic image thereof displayed on the monitor screen, because the optical image of the laser-illuminated biological body portion is optically lost by the laser cut filter.

SUMMARY OF THE INVENTION

The present invention has been made in an attempt to solve the above-described problem of the conventional endoscope apparatus, and therefore has an object to provide a novel electronic endoscope apparatus capable of displaying a laser-illuminated biological body portion and also portions around this laser-illuminated portion without any halation phenomenon.

Briefly stated, this object of the present invention may be achieved by employing a laser mirror type endoscope apparatus and also a half mirror type endoscope apparatus.

An electronic endoscope apparatus (100:200), according to the present invention, comprises:
  electronic scope unit (10) and a main endoscope unit (20:30) coupled to the electronic scope unit (10), the electronic scope unit (10) including:
  laser mirror means (50) upon which laser light (2) reflected from a body cavity of a biological body under medical examination is incident, for refracting a first light component (2A) having a laser light wavelength of the incident laser light (2) and also for passing therethrough a second light component (2B) having a visible light wavelength other than the laser light wavelength;
  first image sensor means (12A) for receiving the first light component (2A) refracted from the laser mirror means (50);
  second image sensor means (12B) for directly receiving the second light component (2B) passing through the laser mirror means (50) to produce a visible light image signal (12VS); and,
  brightness-lowering means (8) positioned on a light-receiving surface of the first image sensor means (12A), for lowering brightness of the first light component (2A) having the laser light wavelength, thereby producing a laser light image signal (12LS) from the first image sensor means (12A); and,
  The main endoscope unit (20:30) processing both the visible light and laser light image signals (12LS:12VS) to display an endoscopic image of the laser-illuminated body cavity and of a body portion around the laser-illuminated body cavity without any halation phenomenon.

Furthermore, another electronic endoscope apparatus (300), according to the present invention, comprises:
  electronic scope unit (40) and a main endoscope unit (20:30) coupled to the electronic scope unit (40), the electronic scope unit (40) including:
  half mirror means (55) upon which laser light (2) reflected from a body cavity of a biological body under medical examination is incident, for refracting a first light component (32A) having a half light quantity of a light quantity of the incident laser light (2) and also for passing therethrough a second light component (32B) having another half quantity;
  first image sensor means (12A) for receiving the first light component (32A) refracted from the half mirror means (55);
  second image sensor means (12B) for receiving the second light component (32B) passing through the half mirror means (55);
  first optical element means (8:33) positioned on a light-receiving surface of the first image sensor means (12A), for optically processing the first light component (32A) so as to derive a brightness-lowered laser light component, whereby a laser light image signal (32LS) is produced from the first image sensor means (12A); and,
  second optical element means (35) positioned on a light-receiving surface of the second image sensor means (12B), for optically processing the second light component (32B) so as to derive a visible light component having no laser light component of the incident laser light (2), whereby a visible image signal (32VS) is produced from the second image sensor means (12B), and, the main endoscope unit (20:30) processing both the laser image signal (32LS) and visible light image signal (32VS) to display an endoscopic image of the laser-illuminated body cavity and of a body portion around the laser-illuminated body cavity without any halation phenomenon.

BRIEF DESCRIPTION OF THE DRAWINGS

For a better understanding of the present invention, reference is made to the following description in conjunction with the accompanying drawings, in which.

DETAILED DESCRIPTION OF THE PREFERRED EMBODIMENTS

ARRANGEMENT OF FIRST LASER MIRROR TYPE ELECTRONIC ENDOSCOPE APPARATUS

Figure 1:
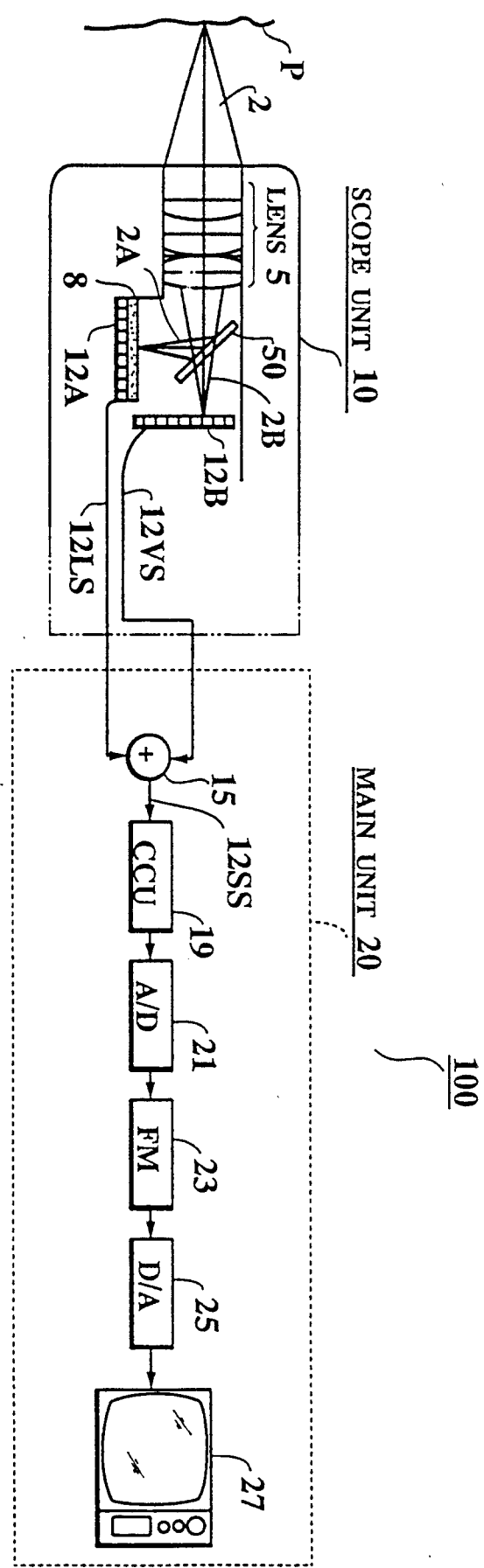
FIG. 1 is a schematic block diagram of an electronic endoscope apparatus 100 employing a laser mirror, according to a first preferred embodiment of the present invention.

FIG. 1 schematically illustrates an arrangement of a laser mirror type electronic endoscope apparatus 100 according to a first preferred embodiment of the present invention. The first laser mirror type electronic endoscope apparatus 100 is mainly constructed of an electronic scope unit 10 and a main endoscope unit 20.

As a major feature of the first preferred embodiment, a laser mirror 50 are positioned within the scope unit 10 in such a manner that laser reflection light 2 which has been produced from, e.g., a YAG (Yttrium Aluminum Garnet) laser and passed through an object lens unit 5, is incident upon the laser mirror 50 and a first light component 2A having a laser wavelength is refracted from this laser mirror 50 and a second light component 2B having a visible light wavelength except for the laser wavelength component passes through this laser mirror 50. The first laser light component 2A refracted from the laser mirror 50 is received via an ND (neutral density) filter 8 by a first CCD (change-coupled device) image sensor 12A, whereas the second visible light component 2B passing through the laser mirror 50 is received by a second CCD image sensor 12B. A light receiving surface of the first CCD image sensor 12A is positioned parallel to a longitudinal direction of the electronic scope unit 10, whereas another light receiving surface of the second CCD image sensor 12B is positioned perpendicular to the longitudinal direction of the electronic scope unit 10.

On the other hand, the main unit 20 includes a series circuit arrangement of a signal synthesizer 15, a camera control unit (CCU) 19, an analog-to-digital (A/D) converter 21, a frame memory (FM) 23, a digital-to-analog (D/A) converter 25, and also a monitor unit 27.

The signal synthesizer 15 synthesizes a first laser-light image signal 12LS derived from the first CCD image sensor 12B with a second visible-light image signal 12VS to produce a synthesized image signal 12SS. Upon receipt of this synthesized image signal 12SS, the camera control unit 19 converts this image signal 12SS into a corresponding NTSC color television signal. The converted color TV signal is analog-to-digital-converted by the A/D converter 21 into color TV signal data so as to be temporarily stored into the frame memory 23 as a still endoscopic image. Then, this color TV signal data are read out from this frame memory 23 and converted by the D/A converter 25 so as to be displayed on the monitor unit 27.

It should be noted that the above-described "laser mirror" is such a narrow pass band reflection mirror known in the optical field.

OPERATION OF FIRST LASER MIRROR TYPE ENDOSCOPE

In the first laser mirror type electronic endoscope apparatus 100, the laser light produced from the YAG laser element (not shown in detail) is projected from the distal end of the electronic scope unit 10 to a surface of a biological body under medical examination such as a patient "P", and the laser light 2 reflected from the laser-illuminated surface thereof is incident upon the laser mirror 50 via the object lens unit 5. The first light component, i.e., laser light component 2A is refracted from the laser mirror 50 and the brightness thereof is attenuated by the ND filter 8 and thereafter incident upon the first CCD image sensor 12A, whereby the first laser-light signal 12LS is outputted from this image sensor 12A. On the other hand, the light component other than the laser light component, i.e., second visible-light component 2B passes through the laser mirror 50 and is incident upon the second CCD image sensor 12B to produce the second visible-light image signal 12VS.

As a consequence, in accordance with the first laser mirror type electronic endoscope apparatus 100, since the laser reflection light 2 is received by the first CCD image sensor 12A after the brightness thereof has been lowered by the ND filter 8, both of the brightnesses of the light incident upon the first and second CCD image sensors 12A and 12B are adjusted to be substantially equal to each other. In other words, the laser reflection light 2 from the patient "P" may be received by the first CCD image sensor 12A at the substantially same brightness as that of the visible light reflected from any portions other than the laser-illuminated portion of the patent "P", which is received by the second CCD image sensor 12B. Thus, the first laser-light image signal 12LS is synthesized with the second visible-light image sensor 12VS in the signal synthesizer 15. When the endoscopic image of the laser-illuminated patient "P" is displayed on the monitor 27 in response to the synthesized image signal 12SS, the laser-illuminated portion of the patient "P" may be directly observed with other portions thereof around this laser-illuminated portion under such a condition that the second visible-light image signal 12VS is not neglected due to the higher brightness of the laser light component, whereby no halation phenomenon may occur in the finally obtained endoscopic image displayed on the display unit 27.

SECOND LASER-MIRROR TYPE ELECTRONIC ENDOSCOPE

Figure 2:
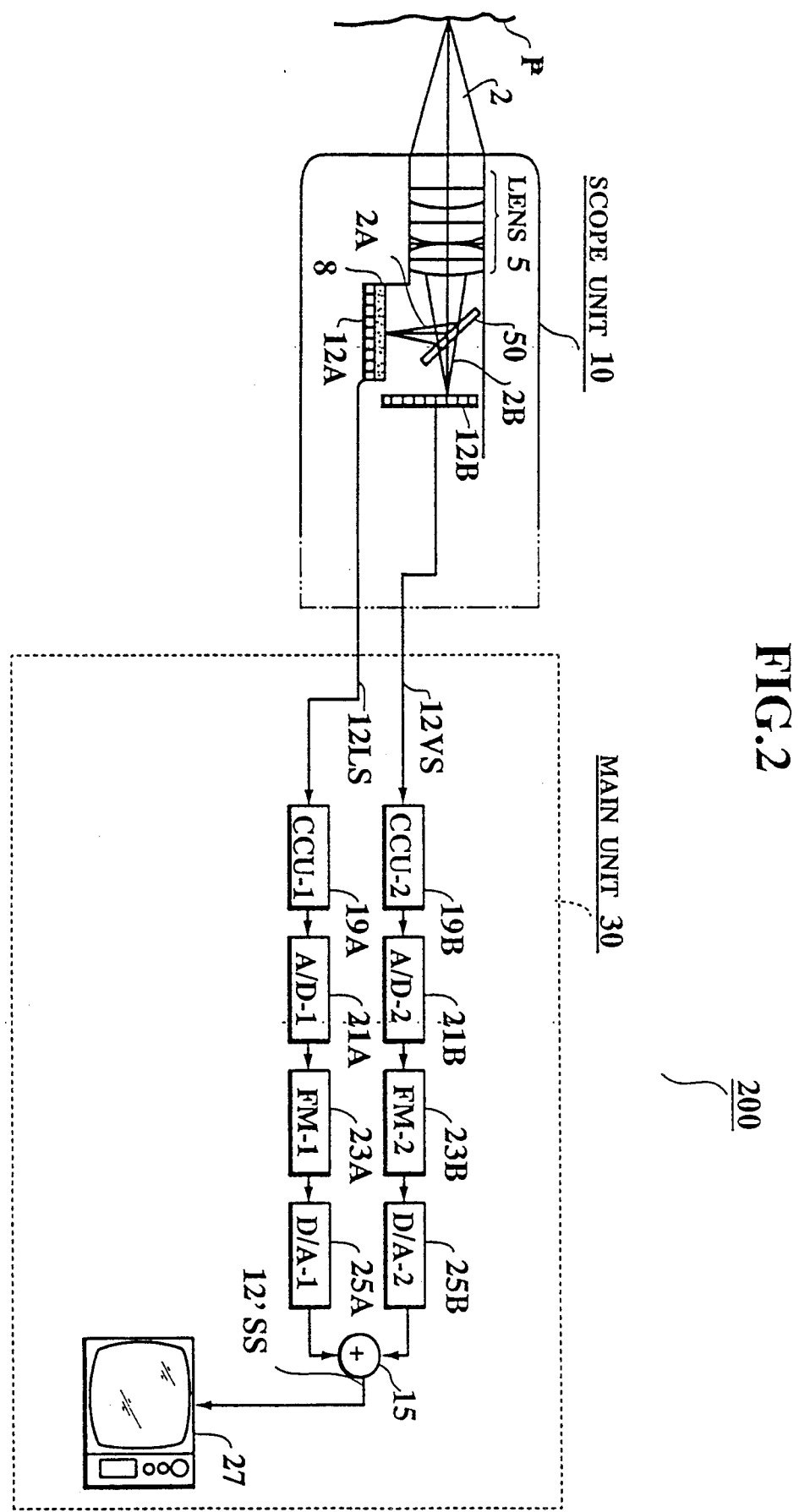
FIG. 2 is a schematic block diagram of another electronic endoscope apparatus 200 employing a laser mirror, according to a second preferred embodiment of the present invention.

FIG. 2 schematically illustrates an arrangement of another laser mirror type electronic endoscope apparatus 200 according to a second preferred embodiment of the present invention.

As apparent from FIG. 2, the construction of the scope unit 10 of the second laser mirror type electronic endoscope apparatus 100 is completely identical to that of the first laser mirror type electronic endoscope apparatus 100, and a main unit 30 thereof is similar to that of the first laser mirror type endoscope apparatus 100. That is, there are employed two sets of series image signal processing circuits. Each of these image signal processing circuits is constructed of, for instance, a camera control unit 19A, an A/D converter 21A, a frame memory 23A and a D/A converter 25A. Two image signals outputted from the first and second D/A converters 25A and 25B are synthesized in a signal synthesizer 15 to obtain a synthesized endoscopic image signal 12'SS. Thus, the desired endoscopic image of the patient "P" directly illuminated by the laser light may be similarly displayed on the monitor unit 27 in response to this synthesized endoscopic image signal 12'SS.

Since other circuit operations of the second laser mirror type electronic endoscope apparatus 200 are the same as those of the first laser mirror type endoscope apparatus 100, no further detailed explanation is made in the following description.

ARRANGEMENT OF THIRD HALF MIRROR TYPE ENDOSCOPE

Figure 3:
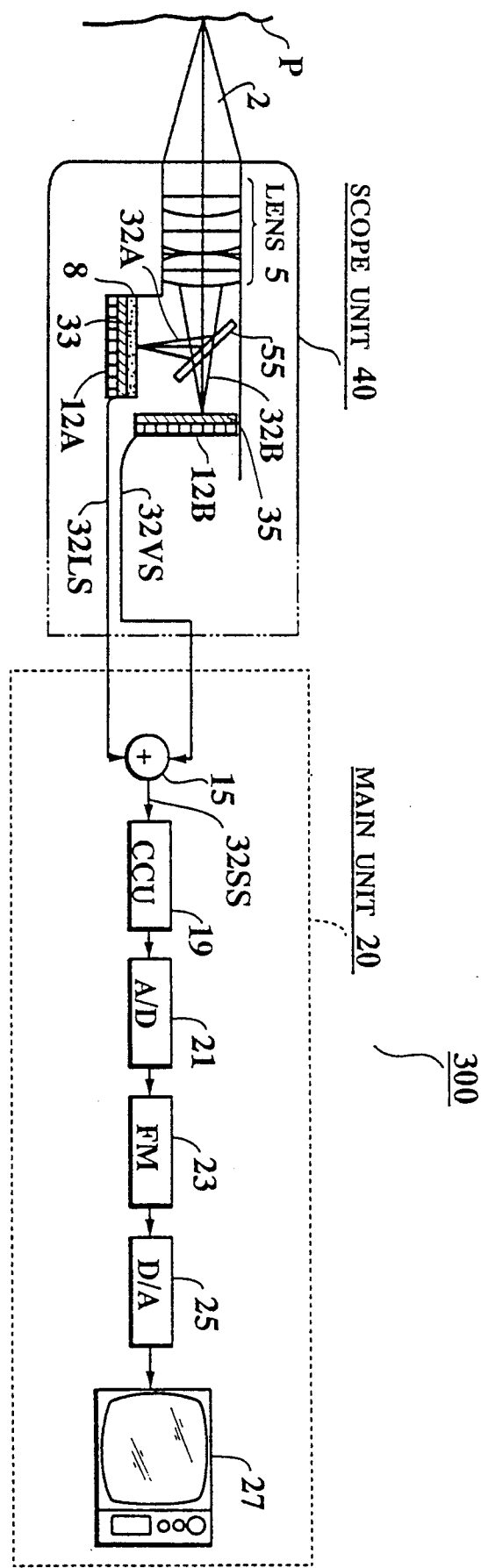
FIG. 3 is a schematic block diagram of a further electronic endoscope apparatus 300 employing a half mirror, according to a third preferred embodiment of the present invention; and, FIG. 4 is a graphic representation of a relationship between transmittance and light wavelengths with respect to the third half mirror type electronic endoscope apparatus 300 shown in FIG. 3.

FIG. 3 schematically represents an arrangement of a electronic endoscope apparatus 300 employing a half mirror, according to a third preferred embodiment of the present invention.

It should be noted that the same reference numerals shown in FIGS. 1 and 2 are employed for denoting the same or similar circuits and components in the third half mirror type electronic endoscope apparatus 300. As apparent from FIG. 3, since the internal circuit arrangement of the main unit 20 is completely identical to that of the first preferred embodiment shown in FIG. 1, no further explanation thereof is made in the following description.

Figure 4:
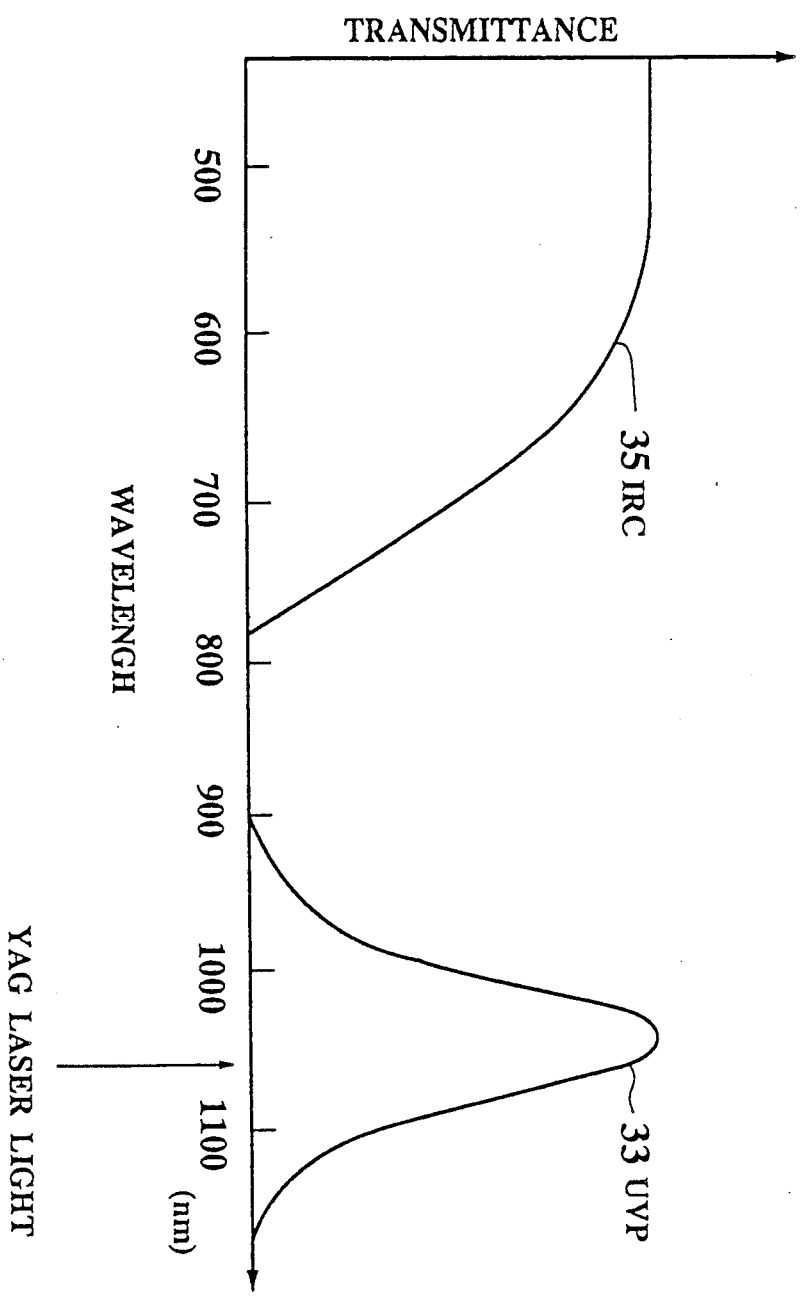

A major feature of the third half mirror type electronic endoscope apparatus 300 is to employ a scope unit 40. That is, this scope unit 40 newly employs a half mirror 55 at a position where the previous laser mirror 50 was located in the first and second endoscope apparatuses 100 and 200. The laser light 2 reflected from the surface of the patient "P" passes through the object lens unit 5 and then is incident upon this half mirror 55. Then, a half amount of the incident laser light 2 is refracted from this half mirror 55 as a laser light component 32A, and also another half amount of this incident laser light 2 passes through this half mirror 55 as a laser light component 33B. On the light receiving surface of the first CCD image sensor 12A, there are provided the ND filter 8 and a bandpass filter 33 having such a transmittance as indicated by "33 UVP" in a graphic representation of FIG. 4. On the other hand, an infrared cut filter 35 having such a transmittance as represented by "35 IRC" in FIG. 4 is positioned on the light receiving surface of the second CCD image sensor 12B. The filter characteristics of these filters 33 and 35 depend upon a wavelength of a YAG laser, e.g., 1,064 nm.

OPERATIONS OF THIRD HALF MIRROR TYPE ENDOSCOPE

In accordance with the third half mirror type endoscope apparatus 300, only a visible light component produced by infrared-cutting out the laser light component 32B which has passed through the half mirror 55 may be received by the second CCD image sensor 12B, whereas a final laser light component produced by neutralizing and bandpass-filtering the laser light component 32A which has be refracted by the half mirror 55. Since the density of the laser light component 32A is neutralized by the ND filter 8, a first laser light image signal 32LS is synthesized with a second visible light signal 32VS and the resultant synthesized light signal 32SS is further processed for the endoscopic image representation, whereby a similar particular advantage to that of the first and second preferred embodiments can be achieved.

MODIFICATIONS

As apparent from the foregoings, the present invention is not limited to the above-described preferred embodiments, but may be readily changed, modified, and substituted without departing from the technical scope of the present invention.

For instance, the position of the synthesizer 15 is not restricted to the first and second preferred embodiments, but may be interposed between the A/D converter 21 and frame memory 23, or between the frame memory 23 and D/A converter 25.

Moreover, the ND filter 8 may be interposed between the bandpass filter 33 and first CCD image sensor 12A. Also, any lasers other than the YAG laser may be utilized, depending upon a sensitivity of an image sensor employed in the electronic endoscope apparatus.

In the half mirror type electronic endoscope apparatus 300 shown in FIG. 3, the infrared cut filter 35 may be positioned on the light incident surface of the first CCD image sensor 12A, whereas a combination of the ND filter 8 and bandpass filter 33 may be positioned on the light incident surface of the second CCD image sensor 12B.

As previously described in detail, in accordance with the laser mirror type and also half mirror type electronic endoscope apparatuses of the present invention, both the laser light directly reflected from the laser-illuminated portion of the biological body under medical examination and the visible light reflected from the portion around the above-described laser-illuminated portion can be received at the substantially same light amounts, or brightness levels by the first and second image sensors. As a consequence, since both of the first and second image signals are synthesized with each other for the endoscopic image display purposes, not only the endoscopic image of the portion around the laser-illuminated biological body portion, but also the endoscopic image of the laser-illuminated biological body can be cleanly observed on the monitor screen.

What is claimed is:

1. An electronic endoscope apparatus comprising:
   electronic scope unit and a main endoscope unit coupled to the electronic scope unit, the electronic scope unit including:
   laser mirror means upon which laser light reflected from a body cavity of a biological body under medical examination is incident, for refracting a first light component having a laser light wavelength of the incident laser light and also for passing therethrough a second light component having a visible light wavelength other than the laser light wavelength;

first image sensor means for receiving the first light component refracted from the laser mirror means;

second image sensor means for directly receiving the second light component passing through the laser mirror means to produce a visible light image signal; and, brightness-lowering means positioned on a light-receiving surface of the first image sensor means, for lowering brightness of the first light component having the laser light wavelength, thereby producing a laser light image signal from the first image sensor means; and, The main endoscope unit processing both the visible light and laser light image signals to display an endoscopic image of the laser-illuminated body cavity and of a body portion around the laser-illuminated body cavity without any halation phenomenon.

2. An electronic endoscope apparatus as claimed in claim 1, wherein said laser mirror means is a laser mirror, and said brightness-lowering means is an ND (neutral density) filter.

3. An electronic endoscope apparatus as claimed in claim 1, further comprising an object lens unit through which said laser light reflected from the laser-illuminated body cavity passes, said laser light being incident upon the laser mirror means through the object lens unit.

4. An electronic endoscope apparatus as claimed in claim 1, wherein said main endoscope unit includes a signal synthesizer for synthesizing the laser light image signal with the visible light image signal to produce a synthesized endoscopic image signal.

5. An electronic endoscope apparatus as claimed in claim 4, wherein said synthesized endoscopic image signal is converted into a corresponding color image signal by a camera control unit and the resultant color image signal is temporarily stored in a frame memory.

6. An electronic endoscope apparatus as claimed in claim 4, wherein said laser light image signal is converted into a first endoscopic image signal by a first camera control unit, said visible light image signal is converted into a second endoscopic image signal by a second camera control unit, and both said first and second endoscopic image signals are synthesized with each other to produce a synthesized endoscopic image signal.

7. An electronic endoscope apparatus comprising:

electronic scope unit and a main endoscope unit coupled to the electronic scope unit, the electronic scope unit including:

half mirror means upon which laser light reflected from a body cavity of a biological body under medical examination is incident, for refracting a first light component having a half light quantity of a light quantity of the incident laser light and also for passing therethrough a second light component having another half quantity;

first image sensor means for receiving the first light component refracted from the half mirror means;

second image sensor means for receiving the second light component passing through the half mirror means;

first optical element means positioned on a light-receiving surface of the first image sensor means, for optically processing the first light component so as to derive a brightness-lowered laser light component, whereby a laser light image signal is produced from the first image sensor means; and, second optical element means positioned on a light-receiving surface of the second image sensor means, for optically processing the second light component so as to derive a visible light component having no laser light component of the incident laser light, whereby a visible image signal is produced from the second image sensor means, and, the main endoscope unit processing both the laser image signal and visible light image signal to display an endoscopic image of the laser-illuminated body cavity and of a body portion around the laser-illuminated body cavity without any halation phenomenon.

8. An electronic endoscope apparatus as claimed in claim 7, wherein said first optical element means includes:

an ND (neutral density) filter for lowering brightness of the first light component refracted from the half mirror means; and, a bandpass filter for filtering the brightness-lowered first light component to obtain said brightness-lowered laser light component; and, said second optical element means includes an infrared cut filter for filtering the second light component to obtain said visible light component having no laser light component of the incident laser light.

9. An electronic endoscope apparatus as claimed in claim 7, further comprising an object lens unit through which said laser light reflected from the laser-illuminated body cavity passes, said laser light being incident upon the laser mirror means through the object lens unit.

10. An electronic endoscope apparatus as claimed in claim 7, wherein said main endoscope unit includes a signal synthesizer for synthesizing the laser light image signal with the second visible light image signal to produce a synthesized endoscopic image signal.

11. An electronic endoscope apparatus as claimed in claim 10, wherein said synthesized endoscopic image signal is converted into a corresponding color image signal by a camera control unit and the resultant color image signal is temporarily stored in a frame memory.

12. An electronic endoscope apparatus as claimed in claim 10, wherein said laser light image signal is converted into a first endoscopic image signal by a first camera control unit, said visible light image signal is converted into a second endoscopic image signal by a second camera control unit, and both said first and second endoscopic image signals are synthesized with each other to produce a synthesized endoscopic image signal.

* * * * *